(12) United States Patent
Hammond

(10) Patent No.: US 11,014,005 B2
(45) Date of Patent: May 25, 2021

(54) DETECTING CHEATING AND CHANGES IN PLAYING ABILITY IN PARTIAL KNOWLEDGE AND TRICK-TAKING GAMES

(71) Applicant: Hammond Software, Inc., Alpharetta, GA (US)

(72) Inventor: Nicolas Hammond, Alpharetta, GA (US)

(73) Assignee: Nicolas Hammond, Alpharetta, GA (US)

( * ) Notice: Subject to any disclaimer, the term of this patent is extended or adjusted under 35 U.S.C. 154(b) by 0 days.

(21) Appl. No.: 16/299,105

(22) Filed: Mar. 11, 2019

(65) Prior Publication Data

US 2019/0336865 A1 Nov. 7, 2019

Related U.S. Application Data

(60) Provisional application No. 62/641,221, filed on Mar. 9, 2018.

(51) Int. Cl.
| | |
|---|---|
| *A63F 13/00* | (2014.01) |
| *A63F 9/24* | (2006.01) |
| *A63F 13/75* | (2014.01) |
| *A63F 13/798* | (2014.01) |
| *A61B 5/16* | (2006.01) |
| *A61B 5/00* | (2006.01) |

(52) U.S. Cl.
CPC .............. *A63F 13/75* (2014.09); *A61B 5/164* (2013.01); *A61B 5/4088* (2013.01); *A63F 13/798* (2014.09); *A63F 2300/558* (2013.01); *A63F 2300/5586* (2013.01)

(58) Field of Classification Search
CPC .. A63F 13/75; A63F 13/798; A63F 2300/558; A63F 2300/5586; A61B 5/164
See application file for complete search history.

(56) References Cited

U.S. PATENT DOCUMENTS

| | | | |
|---|---|---|---|
| 10,427,048 B1* | 10/2019 | Lundquist | ............... A63F 13/75 |
| 2002/0072407 A1* | 6/2002 | Soltys | ................. G07F 17/3241 463/29 |
| 2006/0151955 A1* | 7/2006 | Yarinich | ............. A63F 3/00157 273/292 |
| 2006/0247036 A1* | 11/2006 | Shigeta | ..................... A63F 1/18 463/29 |
| 2006/0247038 A1* | 11/2006 | Bamberger | ............. A63F 13/79 463/29 |
| 2007/0238502 A1* | 10/2007 | Pokorny | ................. G07F 17/32 463/12 |
| 2009/0113554 A1* | 4/2009 | Zalewski | ................ G06F 21/50 726/26 |

(Continued)

*Primary Examiner* — Milap Shah
(74) *Attorney, Agent, or Firm* — Clayton, McKay & Bailey, PC

(57) ABSTRACT

Examples herein include systems for detecting cheating in card games, including bridge. The system can acquire board data for multiple events, the events including bridge games. For each event, determining performance values for a player based on the board data, wherein the performance values may additionally be based in part on timing data. The system can detect a deviation of by comparing the performance values against a threshold, wherein the threshold is based on past performance of known cheating players. Then the system can alert a user when the likelihood of cheating exceeds a threshold.

20 Claims, 9 Drawing Sheets

(56) References Cited

U.S. PATENT DOCUMENTS

| | | | |
|---|---|---|---|
| 2011/0201397 A1* | 8/2011 | Tseng | A63F 1/18 463/11 |
| 2013/0288785 A1* | 10/2013 | Arnone | G07F 17/3241 463/25 |
| 2014/0243077 A1* | 8/2014 | Choi | A63F 13/75 463/29 |
| 2014/0357355 A1* | 12/2014 | Ren | A63F 13/30 463/29 |
| 2015/0290527 A1* | 10/2015 | Shigeta | A63F 1/02 273/149 R |
| 2018/0182208 A1* | 6/2018 | Liu | G07F 17/3239 |
| 2018/0268648 A1* | 9/2018 | Shigeta | G07F 17/3232 |
| 2019/0060738 A1* | 2/2019 | Riordan | A63F 1/12 |

* cited by examiner

```
                    N SCHWARTZ          W    N    E    S
    17              ♠ AK6                    P   1NT   P
                    ♥ K953              P    P
                    ♦ 7542
                    ♣ 102
 W CHARLSEN                             E HOFTANISKA
 ♠ J974                                 ♠ 52
 ♥ AQ                                   ♥ J64
 ♦ AQJ3                                 ♦ 986
 ♣ A84                                  ♣ KJ975
                    S FISHER
                    ♠ Q1083
Other table: 1NT+2  ♥ 10872
NS ISRAEL    0 IMPs ♦ K10
EW NORWAY    0 IMPs ♣ Q63               1NT E           NS: 0 EW: 0
```

FIG. 7

DETECTING CHEATING AND CHANGES IN PLAYING ABILITY IN PARTIAL KNOWLEDGE AND TRICK-TAKING GAMES

CROSS REFERENCE TO RELATED APPLICATION

This application claims priority to provisional patent application No. 62/641,221 ("Detecting Cheating in Partial Knowledge and Trick-Taking Games and Tournaments"), filed Mar. 9, 2018, which is incorporated by reference in its entirety. Mar. 9, 2019, fell on a Saturday, extending the period for filing a non-provisional to Mar. 11, 2019.

BACKGROUND

Bridge is a partnership, partial knowledge, trick taking card game. It is illegal in Bridge to share information about your hand with your partner other than through making legal calls (e.g., bids, passes, double, and redouble) or playing cards. Transfer of illegal information is known as collusive cheating—both parties in a partnership participate. Bridge has had five (5) major scandals between 2013-2015 of top level pairs involved in collusive cheating. All were shown to be cheating through video evidence and decoding their illegal signals. Knowledge that decoding of simple codes has happened will cause pairs that wish to cheat to use non video-detectable methods, such as varying their signals in a pre-arranged, but unknown to any decoder, manner. This patent shows how detection can be done without video evidence. To use correct statistical terminology, this patent shows the statistical likelihood of a pair achieving results within statistical norms. In other words, deviation from these statistical norms are highly indicative of cheating and the level of the likelihood of this occurring can be deduced by statistical methods. By the same manner, tracking of statistics can be used to rate players based on ability. Bridge can be broken down into 4 phases which can be independently measured. Collusive cheating can occur during any of these phases. The phases are bidding, opening lead, play of hand for defenders, play of hand for declarer. Examples herein describe the aggregation of data, processing of data and generating ratings both from individual aspects of the game and also the totality of the data, to then be able to run statistical methods on these results.

Bridge is one type of a trick-taking game (TTG). Bridge, along with other games such as Hearts and Spades, are examples of trick-taking card games that utilize cards. Other trick-taking games might utilize tile or some other non-card medium for the game.

Bridge is one example of a partial knowledge event. More information becomes available to the players during the play of a single board until the last cards played becomes a full knowledge event.

Detecting cheating in bridge using statistical analysis has been an unsolved problem in Duplicate Bridge since the founding of the modern rules by Harold Vanderbilt in 1925.

SUMMARY

It is to be understood that both the foregoing general description and the following detailed description are exemplary and explanatory only and are not restrictive of the examples, as claimed.

In one example, a server can acquire board data for multiple events, the events including bridge games. In one example, a server acquires board data from one or more bridge game web pages. These can be websites where bridge results are displayed for an event, such as a tournament. An event can have multiple rounds. A round can have multiple matches. Each match can have board data that tracks the bidding and cards played during that match. A hand record can indicate which cards a player had at the beginning of the board. For example, in a tournament each table can have the same hand record. The same hand record can be played many times, in an example.

In one example, the server acquires the hand records and board data by running a crawler that builds a tree of events, rounds, and board data, and parsing the hand records for each event from the bridge game pages. This can include starting at the root web site for the results from an event. The crawler can also extract players, board numbers, a contract, a number of tricks taken, declarer, and an opening lead. A contract can have a level and a strain. The level is the number of tricks to be taken. The strain is one of the four suits (clubs, diamonds, hearts, spades) or no trumps. A declarer is the person trying to make the contract. The board data can include the players at the table, the contract, the declarer, the number of tricks taken, and the hand record. Additional optional board data can include the bidding, the opening lead, the cards played, and timing information (e.g., the time taken to make each call and the time taken to play each card).

For each event, round, or session, the crawler can visit the results page and extract each match. For each match, the crawler can extract the contract, declarer, opening lead, number of tricks, and table result for each board. For each board, the crawler can extract the hand record. These hand records can be stored in an event hierarchy, in an example. The hierarchy can include the players at a table that played the board. For each board, the players, the contract, declarer, number of tricks taken, and hand record can be retrieved by the system. In one example, a graphical user interface ("GUI") can allow a user to display the hand record.

The system can normalize the board data by looking up player names and associating the board data with the correct players. Then, a conversion process can convert the normalized board records into a game format for importing into a processing tool.

The processing tool can then apply a detection function to determine if cheating has occurred. To do this, the processing tool can determine performance data based on the board data. In one example, for multiple boards in each event, the processing tool can determine performance values for a player based on the board data, wherein the performance values may additionally be based in part on timing data. This can include determining performance values for a player pair to which the player belongs. The timing data can include information regarding how long it took for the player make a call or play a card. A call can include making a bid. When a situation occurs where a player should have to think, but because they have unauthorized information they do not wait a commensurate amount of time, this can be factored into weighting scores to exceed cheating thresholds.

The processing tool can detect a deviation by comparing the performance values against a threshold, wherein the threshold is based on past performance of known cheating players. For example, past performance data for cheaters can be compiled into thresholds such that when a metric does not meet the threshold, cheating is indicated. In one example, a detection function can be based on defensive double-dummy ratio ("DDR"). For example, the processing tool can calculate the declarer DDR and defensive DDR. Then the processing tool can enumerate the number of boards on defense and create a chart with a plot of defensive DDR to boards on defense. If the defensive DDR is less than a threshold, then a cheating pair can be indicated. Detection functions can be performed on a board, a player, a partnership, or an event, depending on the example.

In addition, in one example, a detection function can, for each event and boards included in the event, compare North/South ("NS") declarer DDR and East/West ("EW") declarer DDR. If a discrepancy exists, this can indicate possible cheating using the tray or some other cheating mechanism. NS DDR and EW DDR should not deviate from one another beyond a threshold.

If a deviation is detected, the processing tool can alert a user regarding a likelihood of cheating. This can include emailing an administrative user associated with the event in which the cheating was detected.

The examples relate generally to systems for use in partial knowledge and trick-taking games and tournaments, and more specifically to systems and methods that can detect cheating at partial knowledge and trick-taking games and tournaments. This also includes the ability to rate players/partnerships in different aspects of such games. The embodiments also apply to games and tournaments that are partial knowledge events.

BRIEF DESCRIPTION OF THE DRAWINGS

FIG. 7 is an example illustration of a GUI screen for displaying a hand record.

DESCRIPTION OF THE EXAMPLES

Figure 1:
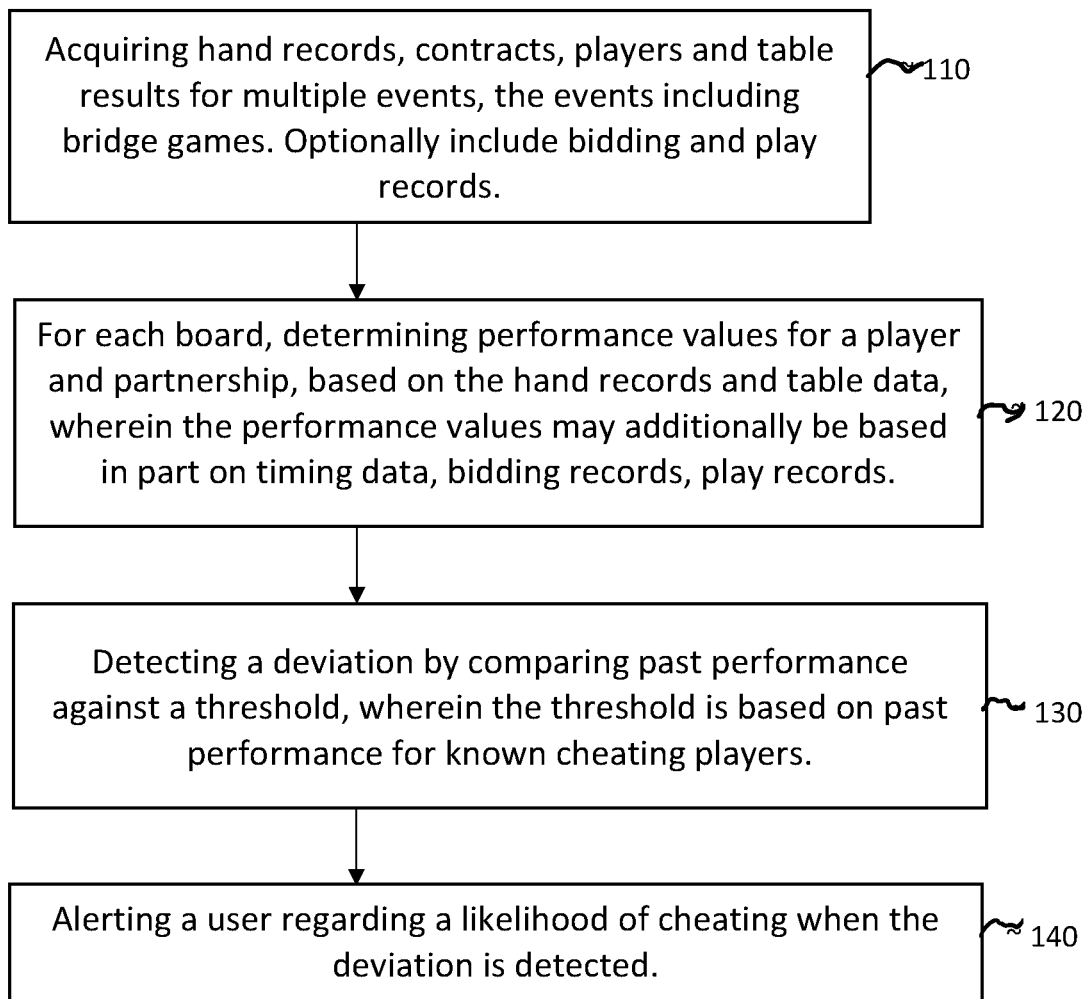
FIG. 1 is an exemplary method of detecting cheating in a game of bridge.

Reference will now be made in detail to the present examples, including examples illustrated in the accompanying drawings. Wherever possible, the same reference numbers will be used throughout the drawings to refer to the same or like parts.

In Bridge, there are events for individuals (rare), pairs (common), and teams of four (common). The scoring is different in pairs and teams. A team of 4 can have up to 6 players on a team with two sitting out at any time (5 is also possible with one player sitting out). There may be multiple scoring methods utilized. For example, in team event the scoring methods may include Swiss, KO, Board-a-Match. Pairs events may use Matchpoint or International Match Points (IMPs) scoring. The scoring affects decisions made by the players during each board. Each board has one of four combinations of "vulnerability"—both sides vulnerable, neither side vulnerable, North-South vulnerable, East-West vulnerable. The vulnerability affects the scoring which affects the decisions that player(s) make.

Events may be broken down into sessions. Each session is typically three or four hours long. An event at a club is typically one session. An event at a tournament is typically one to four sessions long, with two sessions maximum per event per day. National events may have qualifying rounds and are four or six or longer sessions. A typical example might be a national pairs event that starts on Monday and has two sessions. Only the qualifiers from the two sessions on Monday will play on Tuesday, and there are two more sessions on the Tuesday, often with a carryover, that will determine the winners.

During a typical three hour session, approximately 24-27 individual boards will be played, though different time length sessions and different number of boards per session occur.

In a bridge board, each player gets 13 cards. You play with a partner (opposite you). You play against the other pair. These are traditionally assigned to points on the compass, one pair sits North/South, the other pair sits East/West. It is traditional in Bridge to call the latter pair East/West (EW) rather than West/East.

There are three stages to every bridge hand: bidding, playing, scoring. In the bidding, you go in a clockwise order in an auction manner and keep increasing the number of tricks that you think your side can take in a suit contract (or no trumps). After this auction is over, one side has a contract (number of tricks in a suit/no-trumps). In the play of a hand, a player tries to make the contract (or defeat the contract if you are defending). After all tricks are played, declarer has 0 to 13 tricks, and the defenders have the tricks declarer did not take.

Scoring may be complicated, with many different types of scoring dependent on the type of event taking place (Swiss, MP Pairs, IMP Pairs, Board-A-Match, KO just to name a few). A table result may be compared against everyone else who had the same set of cards and scored. Scoring can involve comparing a player's table result with those of teammates, looking up a new scoring number using tables, then converting again to a different number. The scoring impacts the decisions that are made during the bidding/play because the risk/reward for certain actions may change.

Bridge is a partnership game. At a given table, the players sitting North and South (NS) compete against the players sitting East and West (EW). In a Pairs event, each pair competes against the other pairs. In a Team event, one pair from a team will sit NS at one table, and their teammates will set EW at the other table. Their opponents will set EW at the first table and NS at the other table.

In tournament Bridge, the cards are pre-dealt. Usually the hands are generated by a computer algorithm. All tables play the same cards; therefore, there is no luck factor in getting top cards. It matters how well you play the same cards compared to how everyone else is playing the same cards.

It is illegal in bridge to share information with your partner other than through legal calls or through the card that you play to a trick. For example, you may have a legal agreement that a low card in a suit indicates that you like the suit. This information must be disclosed to the opponents. It is illegal to have an agreement, for example, to play a card vertically if you like the suit and horizontally if you do not like the suit.

Since 2013 there have been a number of prominent cheating cases in World Bridge. In one incident a pair was coughing in the Finals of a World Event. An opponent recorded the coughs and there was later found a correlation between the timing of the coughs, the number of the coughs and the hand held by the cougher. In another incident a world class pair was playing a card vertically to indicate an unseen Ace, King or Queen in the suit and horizontally to deny. In another incident, a professional pair was placing the bidding tray in different locations on the table to indicate a preferred suit to lead. In another incident, a professional pair was scratching or touching different body parts to indicate certain cards held in their hand. All these actions are illegal. In all cases the cheating system was discovered and/or later proven through video analysis. Examples disclosed herein render such analysis obsolete, and would have caught the same cheating activity without needing to know the exact method of cheating.

In chess, the current location of all pieces are known to both players. Chess is a full knowledge game. Bridge is a partial knowledge game. During the bidding phase players can only see their own cards. Before the opening lead is made, players can only see their own cards. After the opening lead is faced, one of the four hands is completely faced (referred to as dummy), and the other three players can now see both their own cards and the cards of dummy. The pair that made the highest bid becomes the declaring site. The first person of the declaring side that bid the suit, or bid no-trump if the final contract is in no-trumps, becomes the declarer. Declarer's partner is known as dummy. The person to the left of the declarer makes the opening lead. After the opening lead, dummy faces all of her cards. Dummy takes no further decisions. All of the cards in dummy are called by the declarer. Cards are played face up to each trick. The highest card wins the trick. All players must follow suit. If a player cannot follow suit, she may trump, if the contract is in a suit contract. The highest trump takes the trick if any trump is played. The winner of the trick leads to the next trick. As a trick is played, the players gain more knowledge about the original cards that each player held and also the remaining cards to be played. A skill in bridge is trying to determine who has the remaining cards based on the cards played so far and the original bidding and to determine the best next card to play. A collusive cheating pair can illegal share information about their hands making the problem of defending a hand easier for them.

Bridge is a game of mistakes. Mistakes are defined as the bid or play which, given full knowledge of all hands, does not give up a trick. Analysis of a bridge hand using full knowledge of all cards is known as Double Dummy Analysis (DDA). DDA is trivial on modern computers (well under a second for all cards). For example, DDA can analyze how many tricks a player should take in optimal circumstances (based on the hand record) versus the number that player actually took.

All players make mistakes. Cheating players make fewer mistakes because they have more knowledge of the hands. Detecting cheating is detecting the absence of mistakes. This detection is measurable and quantifiable. The corollary is that it is difficult to prove cheating without a known code and video evidence to support use of the code as a correlation between the code and a player's hand. The reason is that a cheating pair has the potential of making no mistakes. It is hard to prove a cheating instance in the absence of any evidence that a player made the wrong play. Examples herein address this problem.

At a minimum for the collection of data, we need to know the players at the table, the hand record, the final contract, the declarer. Additional data that can be used to generate more statistics includes the opening lead, the bidding, the cards played to each trick. The more data that is available, the better the statistics.

FIG. 1 is an example method for detecting cheating in bridge. At stage 110, a server can acquire board data for multiple events, the events including bridge games. In one example, a server acquires board data from one or more bridge game web pages. These can be websites where bridge results are displayed for an event, such as a tournament. An event can have multiple rounds. A round can have multiple matches. Each match can have board data that tracks the bidding and cards played during that match.

In one example, the server acquires the board data by running a crawler that builds a tree of events, rounds, and board data, and parsing the hand records for each event from the bridge game pages. This can include starting at the root web site for the results from an event. The crawler can also extract players, board numbers, a contract, a number of tricks taken, declarer, and an opening lead. A contract can be the number of tricks taken in a suit or no trumps. A strain is one the suits or no trumps. No trumps can mean nobody won a suit by playing a trump. A declarer is the person trying to make the contract.

For each event, round, or session, the crawler can visit the results page and extract each match. For each match, the crawler can extract the contract, declarer, opening lead, number of tricks, and table result for each board. For each board, the crawler can extract the hand record. The board data can be stored in an event hierarchy, in an example. The hierarchy can include the players at a table that played the board. For each board, the players, the contract, declarer, number of tricks taken, and hand record can be retrieved by the system. In one example, a graphical user interface ("GUI") can allow a user to display the board data.

The system can normalize the board data by looking up player names and associating the board data with the correct players. Then, a conversion process can convert the normalized board data into a game format for importing into a processing tool. The game format can be, for example, XML, JSON, or a custom format for importing into a processing tool. The different forms of the normalized data can be American Contract Bridge League ("ACBL") data, European Bridge League ("EBL") data, World Bridge Federation ("WBF") data, Bridge Base Online ("BBO") data, or other data.

At stage 120, the processing tool can then apply a detection function to determine if cheating has occurred. To do this, the processing tool can determine performance data based on the board data. In one example, for multiple boards in each event, the processing tool can determine performance values for a player based on the board data, wherein the performance values may additionally be based in part on timing data. This can include determining performance values for a player pair (partnership) to which the player belongs. The timing data can include information regarding long it took for the player or pair to make a call or play a card. This can be deduced by comparing time data of each call or play of the card.

At stage 130, the processing tool can detect a deviation of by comparing the performance values against a threshold, wherein the threshold is based on past performance of known cheating players. In one example, a first detection function can, for each board, compare North/South ("NS") declarer DDR and East/West ("EW") declarer double-dummy ratio ("DDR"). If a threshold discrepancy exists, this can indicate possible cheating using the tray or other method. A second detection function can be based on defensive DDR. For example, the processing tool can calculate the declarer DDR and defensive DDR. Then the processing tool can enumerate the number of boards on defense and create a chart with a plot of defensive DDR to boards on defense. If the defensive DDR is less than a threshold, then a cheating pair can be indicated. Detection functions can be performed on a board or a partnership.

If a deviation is detected, at stage 140 the processing tool can alert a user regarding a likelihood of cheating. This can include emailing an administrative user associated with the event in which the cheating was detected.

Figure 2:
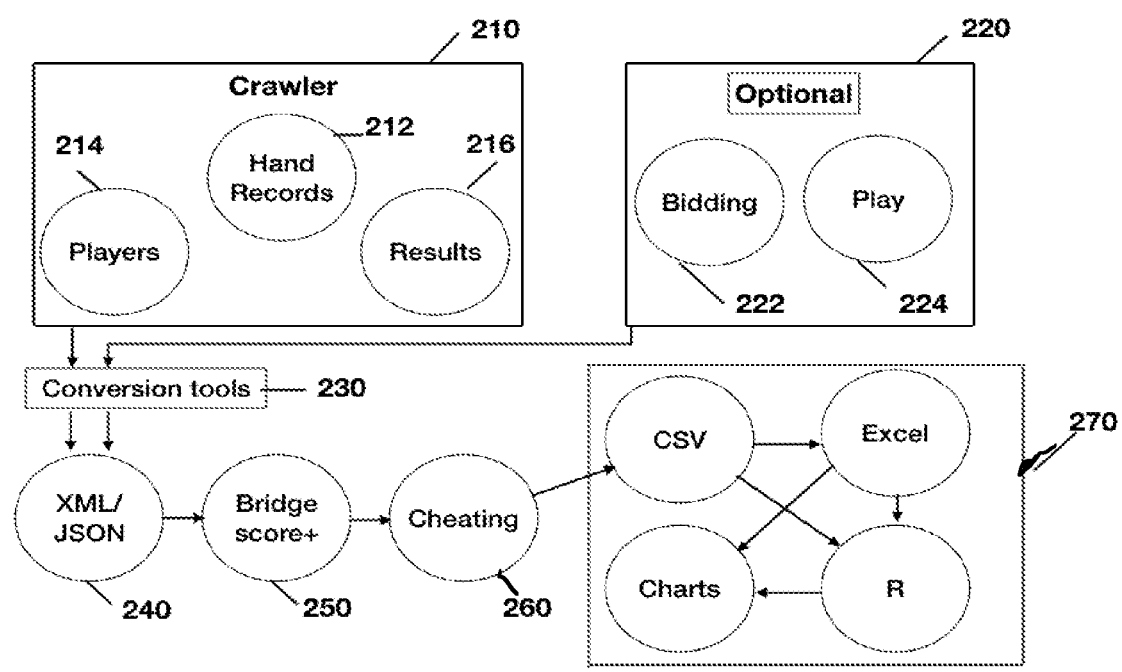
FIG. 2 is an exemplary method of detecting cheating in a game of bridge.

FIG. 2 include method steps performed in an example. For example, at stage 210, a crawler can retrieve player names 214, hand records 212, and game results 216. Optionally, at stage 230, the crawler can also obtain information about bidding 222 and play of the hand 224. For example, required information can include the names of the players, the hand records and the table result (contract, declarer, number of tricks taken. The names of the players is optional if only analysis of the tournament is needed. The names of the players are optionally normalized or converted to a unique identifier for each player. Additional information can be from the bidding and the play of the hand (cards played to each tricks). This may optionally including the timing of each bid and the timing of each card played.

At stage 240, the data can be converted to a standardized XML or JSON format. Any other text-readable format is also possible. This is an optional setting prior to importing to a system, such as the processing tool, for processing. The processing tool can import the data from an XML, JSON or other type of file and stores in a database or other file format.

At stage 250, the processing tool can then perform some pre-processing duties, for example, calculation of double dummy analysis ("DDA"). This can include comparing a player's tricks to theoretical "double dummy" tricks under DDA. The DDA can be redone after each card is played. In one example, anyone above 98.2% is cheating, in an example, because from a statistical standpoint only known cheaters achieve that threshold.

Bridge is a single dummy game (i.e., all players can only see dummy and their own hands). A perfect player would play double dummy (i.e., knowledge of all hands). There are many hands where double dummy play is the opposite of single dummy play. For example, if a player is missing three cards including the king in the trump suit and has AQJ109 in dummy, the player will likely try and finesse the king. The player will occasionally lose to a singleton king offside. Playing double dummy, the player will play the ace and drop the singleton king only when the singleton king is offside. Therefore, we expect double dummy mistakes in a single dummy game. However, we can apply the Law of Large Numbers ("LLN") to state that, for any given partnership, and a large enough sample set of boards, they should expect an equal number of offside kings as other pairs. The same is true if the player has AJ10 opposite K9875. The player will have to guess who has the queen. There may be some information from the bidding but using the LLN the player is expected to have to make the guess as often as other declarers. Under double dummy, the player would always get this right. To give this in its purest form, supposing the player has AJ3 opposite K104. The contract is 7NT. The player is down to the last three tricks. Each of the opponents has three cards in the suit. Who has the queen?

Looking at all the cards played in a hand, on average 3.1% of the time world-class declarers will play the wrong card (according to double dummy). For the same group of players, excluding the opening lead, the average value is 2.3%. This shows the importance of the opening lead.

At stage 260, the processing tool can check for cheating. The system can apply statistical tools to derive the likelihood of a player or pair cheating, based on comparing their ratings to expected norms. The system can examine and rate an individual player's ability to declare the cards. The system can compare two individual player's ability to declare the cards against the two players' ability to defend the cards when playing in a partnership. A correlation between the two is expected. The system can create correlation values and examine using statistical tools to see how the ratings on partnership defense compare to the individual's declarer performance.

In one example, for each board, the processing tool can perform DDA, tracking whether the player performed the play that would have been performed in a double dummy scenario. For each board played, the processing tool can store for each partnership based on declarer/defender. Then the processing tool can perform high level analytics on the board and table result. Then, for each played card, the processing tool can redo DDA and store the result.

In one example, the processing tool performs data aggregation. For each partnership, the processing tool can retrieve data from each board as declarer or defender. Some data can be filtered out based on filter criteria. Optional filtering may include either permitting or denying boards played by set of players or partnerships. For example, filtering can remove all boards played by a partnership convicted of collusive cheating, or only include boards played by a suspected partnership.

The remaining data can be aggregated and stored. For example, the processing tool can do this for all boards within an event. The processing tool can also do this for all events within a tournament. In one example, the information stored for each board can include Board origin data (sufficient data to trace back to original source), Board number, North player, East player, South player, West player, Hand record, Declarer, Contract, Number of tricks taken, Optional information for each board, Bidding, Opening lead, and Play of each card.

During the processing stage, the following information can be calculated and added for each board: DDA showing number of expected tricks in a contract, 52 values for each card played showing DDA, and if the played card loses a trick according to DDA or not.

For tournaments that use screens, the processing tool can evaluate the NS declarer double dummy rate ("DDR"). This can reflect how often an NS pair compares to the contract DDA (the contract DDA is defined as the expected score assuming full knowledge of all cards and each player attempting to maximize the taking of tricks for the partnership). The processing tool can then evaluate the East/West declarer DDR. These can be compared against one another and against historical thresholds for known cheaters. If there is a threshold discrepancy between the North/South and East/West DDR values, this can indicate possible cheating using the tray or other methods. The threshold discrepancy is based on comparison.

One or more such cheating detection functions can be deployed by the processing tool. As another example, the processing tool can take the following steps for each partnership: (a) Calculate the declarer DDR; (b) Calculate the defensive DDR, (c) Enumerate the number of boards on defense, and (d) Create a chart with a plot of defensive DDR to boards on defense. Cheating pairs so far have a defensive DDR of less than 1.05.

As still another example, for each partnership the processing tool can perform stages including: (a) enumerating the number of boards on defense ("DEFN"), (b) enumerating the number of boards as declare ("DECN"), (c) filter out all pairs where DECN>=DEFN, and (d) calculate the defensive DDR. Cheating pairs will, in one example, have a defensive DDR of less than 1.05. Filter out any pairs with a DDR>=1.05 based on past known cheaters. The processing tool can continue by (e) calculating the percentage of played cards on defense that did not give up a trick ("DEFPC"), (f) calculating the percentage of played cards when declaring that did not give up a trick (DECPC), and (g) evaluating PCDIFF=DEFPC−DECPC. Cheating pairs will, in one example, have a defensive DEFPC of greater than 97.85. The processing tool can filter out any pairs with DEFPC<=97.85. The processing tool can then (h) sort by PCDIFF. Pairs likely to be cheating will have PCDIFF>=0.95. The processing tool can then compare to known cheating pairs and sort by DEFPC. Pairs likely to be cheating can have DEFPC>=98.20 based on comparison to known cheating pairs.

The processing tool can further determine if a player is violating a bridge law regarding improper partnership agreements. For example, if 500 boards have been played, and one player has played 65% of the hands (325) and the other player has played 35% of the hands (175) then the probability of this, assuming a 0.5 probability that each player should play each hand is less than 1 in 105,000,000,000. When the probability falls below a threshold, cheating can be flagged.

In still another example, the function can detect signs of mental disease, such as Alzheimer's. For each player, the processing tool can evaluate declarer DDR and defensive DDR as a baseline. Then, the processing tool can consider the last n months of data, where n is a variable depending on the amount of boards player by that person each month. The processing tool can calculate declarer DDR for last n months, and compare that DDR value to previous months, monitoring for sustained or trending negative changes. The processing tool can calculate defense DDR using similar methods; ideally with the same partner and monitor changes. A gradual or sudden change in the DDR values can indicate a loss in playing ability which indicates early detection of loss of mental ability. For example, it can indicate early onset of Alzheimer's.

These functions can cause the processing tool to send an alert or export data. At stage 260, the system can export data or send an alert regarding cheating. The exported data can take a form of a .CSV file, an EXCEL file, charts, or some other form. In one example, the data is converted to a CSV file format, however any file format can be used. The CSV file can be optionally processed by any number of tools. In the example implementation, it shows data being further processed by Excel, or by R, the statistics package. From these additional tools, e.g. Excel, R, charts can be generated.

Figure 3:
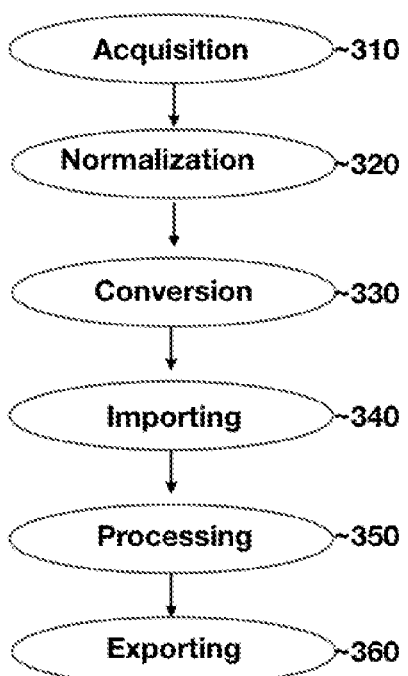
FIG. 3 is an exemplary method of detecting cheating in a game of bridge.

FIG. 3 is an example high-level outline of this process. Data can be acquired at stage 310, normalized at stage 320, converted at stage 330, imported at stage 340, processed (e.g., for cheating or mental disability) at stage 350, and exported (e.g., alerts or reporting) at stage 360.

Figure 4:
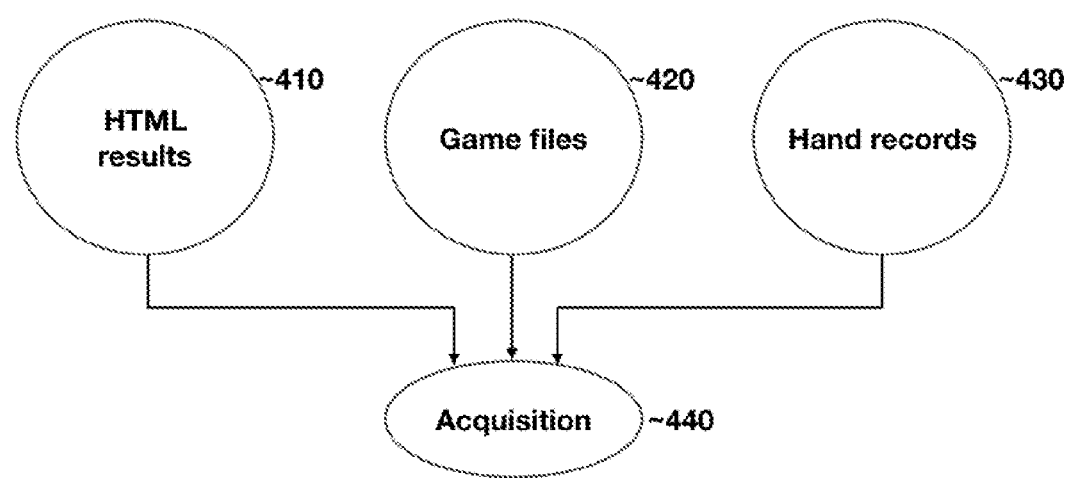
FIG. 4 is an exemplary method for an acquisition step.

FIG. 4 illustrates stages performed for acquisition, in an example. At stage 410, a crawler gathers HTML results from one or more webpages. The results can be from multiple tournaments in order to detect cheating patterns across various events. At stage 420, game files can be gathered, either by the crawler or directly from an event-provider. Similarly, at stage 430, board data including moves and player information, can be gathered by the crawler or from the event-provider directly, such as through an application programming interface ("API").

Figure 5:
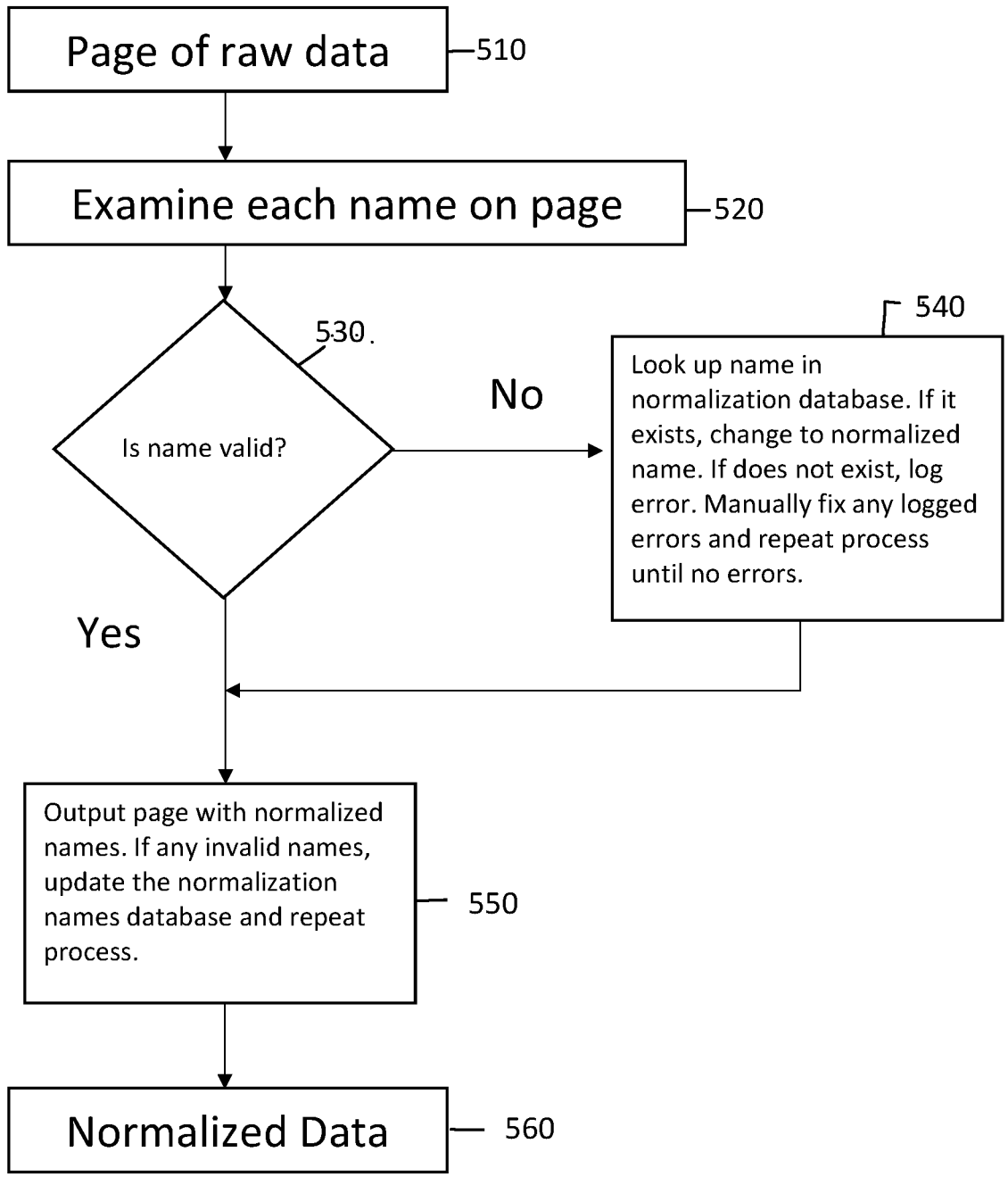
FIG. 5 is an exemplary method for a normalization step.

FIG. 5 illustrates example stages used during normalization. At stage 510, the processing tool can receive a page of raw data. This can be data retrieved by the crawler or from an API call to a server. At stage 520, the processing tool can examine each name, comparing it against a table of existing board data with names. At stage 530, the processing tool can check the validity of the name. This can be manual or automatic. It can include automatically cross referencing membership ID, and contacting an admin if no match is detected. The human admin can then attempt to look up the player.

If the name cannot be found, at stage 540 a normalization database is checked. This can include checking for threshold closeness for first and last names of the player. Close entries can be flagged for inspection and approval by an administrator user. The administrator can manually fix errors, or add a new name to the normalization database for use in future checking. In one example, different iterations of the same name are stored in relation to a normalized version of the name.

At state 550, based on matching a name, the name is normalized and the data is changed to the normalized name. The board data with the normalized name is then used by the processing tool, such as aggregating this information. At stage 560, the normalized data is sent to the processing tool.

Figure 6:
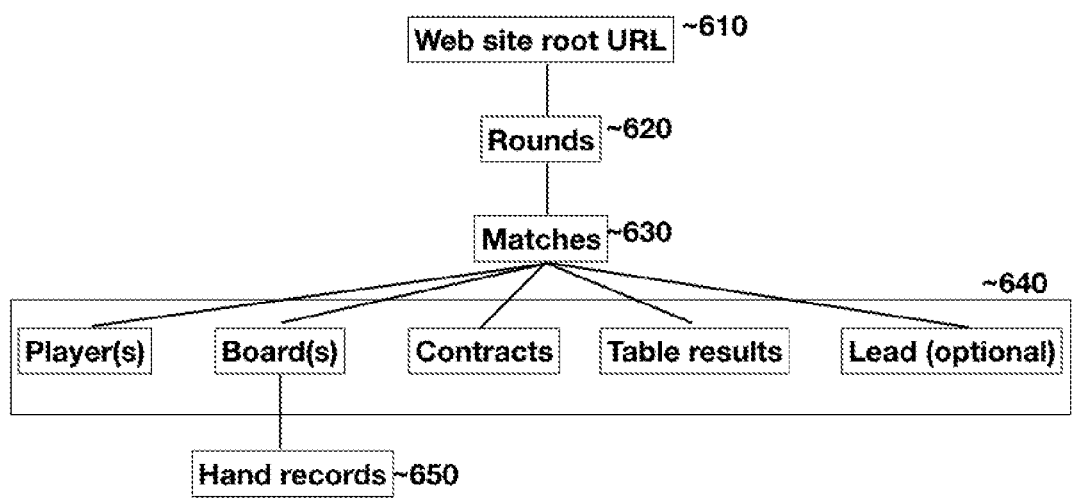
FIG. 6 is an example illustration of a hierarchy constructed by a crawler.

FIG. 6 illustrates an example hierarchy of data collected and used by the processing tool. Each website 610 is crawled for multiple rounds 620, each round for multiple matches 630. Board data 640 is extracted for each match 630. Hand records 650 are extracted as part of the board data 640.

FIG. 7 is an example graphical user interface ("GUI") for displaying board data. In this example, the current hands are illustrated. In one example, each time cards are played, DDR is reanalyzed based on the current hand record.

Figure 8:
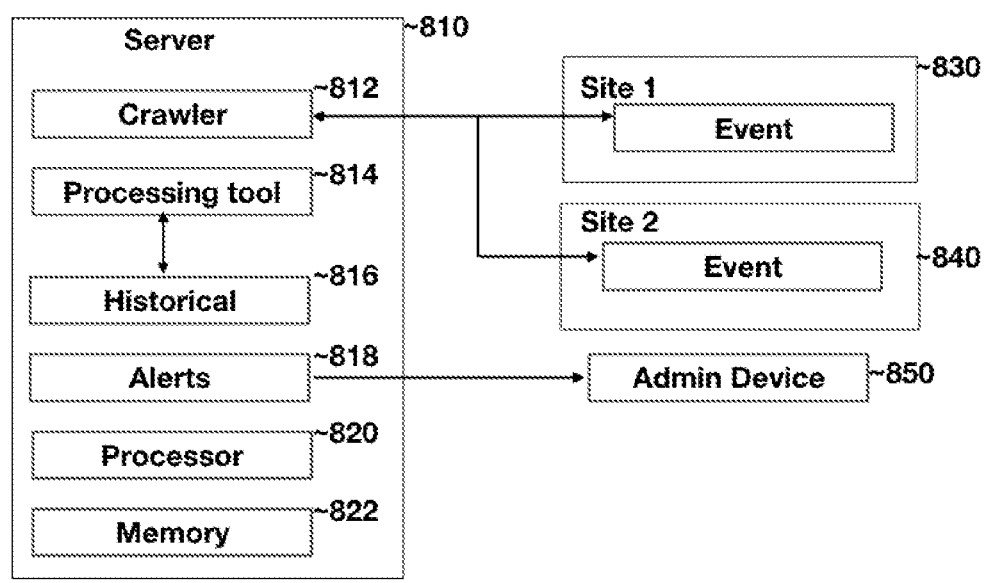
FIG. 8 is an example illustration of system components.

FIG. 8 is an example illustration of system components, in an example. A server 810 can be any processor-equipped device, such as a rack-mounted server, user device, cell phone, laptop, or tablet. The server can include at least one processor 820 that executes instructions in a memory 822. The memory 822 can be any physical storage medium, and can include instructions for detecting cheating.

In one example, the server 812 executes a crawler 812. The crawler 812 can be a software process that executes on the server 812. The crawler 812 can be pointed to several known sites 830, 840 that include event information. Each site 830, 840 can be websites on remote servers, in an example. The crawler 812 can scrape information off of those sites to form the information hierarchy of FIG. 6. In particular, the crawler 812 can retrieve board data used in detecting cheating.

The crawler 812 or another process can access the board data by making an API call in one example. Some servers can provide the board data in a format used by the processing tool 814, or in a format that can be converted for use by the processing tool 814.

A processing tool 814 can be another process that executes on the server 810. In one example, it includes the crawler 812.

The processing tool 814 can use historical board data 816 to determine if a player is cheating, in an example. This can be based on DDR analysis over the history or the player or based on a single event in comparison with the history. Analysis of a partnership can include analysis of a player for purposes of this disclosure.

If the processing tool 814 detects cheating or some mental issue, the processing tool 814 can cause the server 810 to issue an alert. This can include sending an alert to an administrator device 850. The administrator device 850 can be associated with an administrator of an event or bridge organization. The administrator device 850 can be any processor-based device such as a phone, laptop, of tablet. The alert can be an email or an alert on an app on the administrator device 850.

Figure 9:
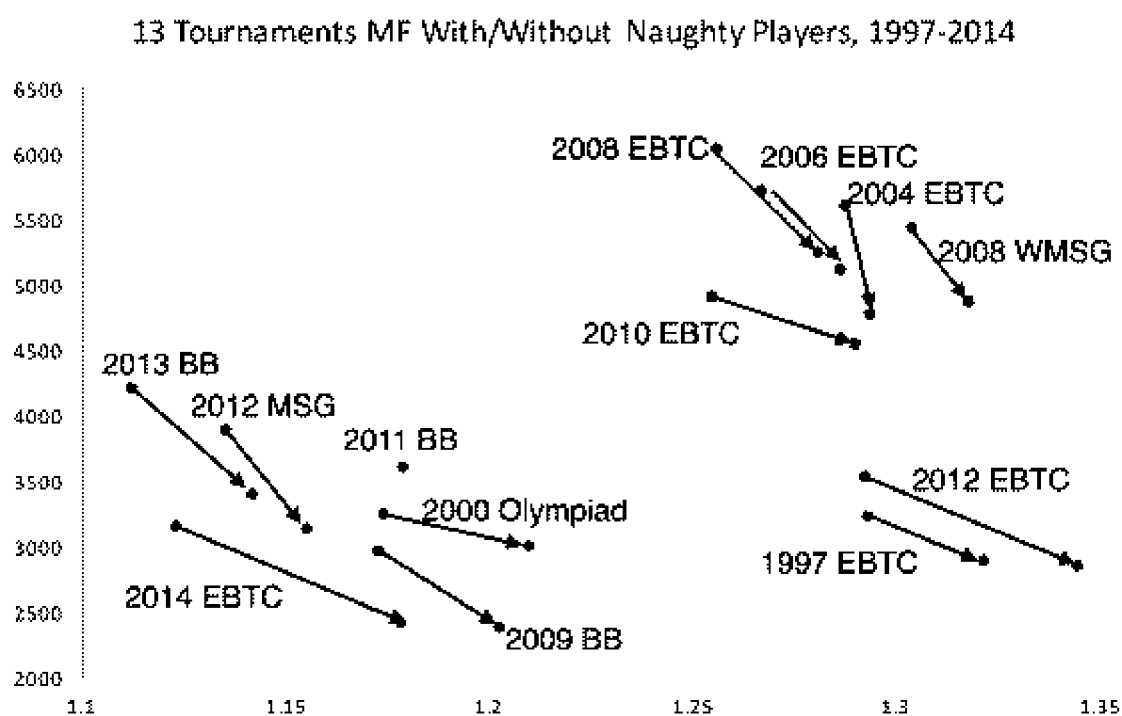
FIG. 9 is an example table showing DDR values.

FIG. 9 is a table showing the DDR values from the top 13 tournaments from 1997-2014. The abbreviations are: BB=Bermuda Bowl, EBTC=European Bridge Team Championship, MSG=Mind Sports Games. The first dot indicates the DDR value with cheating pairs. The arrow indicates the result when the naughty pairs are removed. There are no known naughty pairs that played in the Bermuda Bowl in 2011.

This chart shows how the DDR value works at the tournament level. In all cases, removing the data for a cheating pair increase the DDR value.

Additional Description of Details

Law of Large Numbers

The Law of Large Numbers (LLN) can be applied to Bridge.

LLN is defined as "In probability theory, the law of large numbers (LLN) is a theorem that describes the result of performing the same experiment a large number of times. According to the law, the average of the results obtained from a large number of trials should be close to the expected value and will tend to become closer as more trials are performed." [Wikipedia]

An alternative definition is "The law of large numbers is a principle of probability according to which the frequencies of events with the same likelihood of occurrence even out, given enough trials or instances. As the number of experiments increases, the actual ratio of outcomes will converge on the theoretical, or expected, ratio of outcomes." [Whatis.com]

Consider guessing if a tossed coin will land heads. The probability of a fair coin landing heads is 50% (p=0.5). Ask 1024 people to toss a coin 10 times and record the number of heads that occur. The number 1024 is deliberately chosen because 1024=2^10.

The expected results are well-known. They are part of the Fibonacci series. The results follow the normal distribution. This field of mathematical probability and statistics is well understood. The results are symmetrical, with the average being 5 heads. On average there will be 1 person that reports 0 (or 10) heads, 10 that report 1 (or 9) heads, 45 that report 2 (or 8), 120 that report 3 (or 7), 210 that report 4 (or 6) and 252 that report 5.

The LLN states that the more attempts that are made, the more likely that the results will tend to the expected result. In this case, we know that a fair coin will land on heads 50% of the time. The normal distribution curve becomes more squished as we increase the number of times. The probability of there being 0 total heads (or total tails) decreases by a factor of 2 for each additional coin toss.

The previous three charts show the "squishing effect" and the effect of the LLN as results tend to the average. The likelihood of results on either end of the normal distribution curve decreases as more guesses are made.

Law of Large Numbers—Applied to Bridge

Consider the following 3 card ending in Bridge:

TABLE 1

|  | K J 10 |  |
|---|---|---|
| ? x x |  | ? x x |
|  | A 3 2 |  |

The South hand holds A 3 2, the North hand holds K J 10 where A=Ace, K=King, Q=Queen, J=Jack. The West and East hands each have 3 cards in the suit. One of the West or East hands has the Queen (Q). South wants to take all of the remaining tricks. South does not know which player has the Queen. If West has the Queen, the correct play is to play the Ace, then lead a low card to the remaining K J and cover the card that West plays. Covering the card that West plays is known as taking a finesse. If East has the Queen, the correct play is a low card to the K, then play the J and, if East plays the Queen to play the Ace; if East does not play the Queen, South will play low. This is taking the finesse of the Queen against East.

This is an example of a 50-50 play in Bridge. South, without full knowledge of the missing cards, is expected to guess the location of the Queen 50% of the time. A DDA would guess correctly 100% of the time.

If we find that South consistently guesses the location of the Queen, with a higher probability than 50%, then well-known statistical methods can be applied to determine the probability that this is a random event given the number of correct guesses and the number of incorrect guesses. Collusive cheating could have occurred if the North player had stood up, walked around and looked at either the West or East hand and reported to South through an illegal signal which player possessed the Queen—this actual method has been used by professional bridge players with players being caught and suspended.

Well known statistical methods can be applied to determine the statistical likelihood of a given event occurring m times out of n occurrences with a probability of p.

Scientists use a similar method for randomness in reporting results. For example, CERN reports results when they reach a five-sigma level. The same calculations are well-understood for truly random data.

Mistakes in Bridge

All players make mistakes. Expert players make fewer mistakes than weaker players. Cheating players make fewer mistakes because they have more knowledge of the hands. Detecting cheating is detecting the absence of mistakes. The detection of mistakes is measurable. The difference between cheating and expert play is quantifiable.

Consider the following suit that has to be played in a no-trump contract.

TABLE 2

|  | A K J 10 |  |
|---|---|---|
| ? ? ? ? ? |  | ? ? ? ? ? |
|  | 5 4 3 2 |  |

South does not know the location of the missing 5 cards in the suit. The correct way to play this suit to maximize the number of tricks that South can take is to cash the Ace to cater for a singleton Queen in the East hand, then, assuming sufficient transportation, i.e. the ability to cross to the South hand, to take multiple finesses of the Queen against West. South will always fail to take 4 tricks if East holds the Queen and two or more cards. However, in the situation where East has two cards, one of which is the Queen, the double dummy analysis would show that North should play the Ace and then the King. This is anti-percentage. Occasionally there is bridge logic for this play (East has bid indicating values and therefore is more likely to have the Queen), but this is rare. The single-dummy percentage of taking 4 tricks with this hand combination is more than 50% because of the possibility of a singleton Queen with East. The difference between double dummy play and single dummy play can be quantified. Using the LLN the randomness of the hand patterns that each pair faces averages out over time.

Each card combination has a different probability of correct single-dummy play and correct double dummy play. Each card combination may have a different actual probability based on previous bidding and play. With a large data set of hands played, the LLN applies and the randomness of particular cards in a particular hand is averaged out.

Using the card example above, there will be occasions when East has Queen and one card (known as Queen doubleton) and South makes the correct double-dummy play of the Ace and then the King. However, statistically over time, South is expected to make the normal single dummy play and occasionally lose one trick to the Queen doubleton with East. The LLN applies assuming a large data set.

All cheating players make mistakes against DDA. If a player was completely error free when compared to DDA this would be detected very quickly and reported by their opponents. Consider the following suit that has to be played in a no-trump contract.

TABLE 3

|   |   |   |
|---|---|---|
|   | A Q J 10 |   |
| x x x x |   | K |
|   | 5 4 3 2 |   |

The correct single-dummy play, assuming sufficient transportation, is to take four finesses against West. The correct double dummy play is to cash the Ace and drop the singleton King. The statistical likelihood of East having a singleton, and it being a singleton King, is sufficiently small that if a player that made this play, without a valid bridge reason, the play is likely to be reported immediately as cause for cheating.

Mistakes on defense are more common. For example, during the play of a hand you may need to pick one of three suits at trick 3 to lead to set the contract. If you happen to pick the correct one of the three at the table, you are not likely to be reported to be cheating. The likelihood of you guessing correctly is ⅓. Over time, defensive players are faced with these decisions multiple times.

Examples herein apply to the ability to collect large quantities of data about bridge hands, convert them to a format suitable for processing, store them in electronic format, process the results to generate the data and examine the results using statistical tools.

There are multiple formulae that can be applied to different aspects of a game.

There are four separate phases to a bridge hand where cheating can occur. The bidding, the opening lead, the defender play, the declarer play. For each phase, there are multiple formulae that can be used to generate a rating of a player/partnership.

Bridge Phase—General

Different statistics apply within the different phases, however there are some general rules that apply to all phases. Bridge scoring has an impact. For some events, the Bridge scoring awards aggressive bidding and play, therefore adjustments may need to be made for the type of scoring in effect.

Comparison of data can be made using DDA or using actual table results. Methods of comparison data can include simple enumeration or more complicated calculations based on the type of scoring in effect for that board.

One method is a simple enumeration of the number of times that an event occurs. For example, in bidding it could be a comparison against par. For card play, it could be a comparison of the final number of tricks taken against the expected number of tricks available through double dummy. In both cases, the enumeration is based on greater than, equal to, less than.

More complex calculations involve using a Bridge scoring conversion table that converts a table result to an International Match Point (IMP) scale. IMPs are typically used for scoring Bridge team events, therefore for events with this type of scoring, the comparison of a result to double dummy then a conversion using the IMP scale may be more meaningful than a simple enumeration. For example, the risk/reward of defeating a contract that promises to take all 13 tricks is much higher than defeating a contract that only promises to take 7 tricks. If we assume the basic premise that cheating pairs do not want to get caught, they will only want to cheat on hands with a large reward compared to the risk of being caught. Therefore, they may choose to cheat on 13 trick contracts, but not on 7 trick contracts, as the risk/reward ratio is much higher.

Bridge Phase—Bidding

Ratings can be created at the completion of the bidding phase to correlate the final contracts against par. Par is defined as the best possible contract/table result for all pairs assuming full knowledge. Par is generated by DDA tools. The DDA tools can also generate the table result given a certain contract assuming perfect play by all players.

Comparison against par can be done using a variety of methods. For example, the DDA table result could be used, or the actual table result could be used. Bridge scoring has an impact on bidding. For some events, the Bridge scoring awards aggressive bidding, therefore adjustments may need to be made for the type of scoring in effect.

Other options include looking at the number of tricks that should be taken based on the final contract. One method is a simple enumeration of the number of times that the partnership bid to par, better than par, or worse than par. Better than par would occur if the opponents overbid and reached a non-makeable contract that award a better table result than par. This is a generalized method that works for all types of scoring.

Other methods are better for specific types of scoring. For example, one method is the comparison of the DDA table result against par. For events scored using IMPs, the difference between the table result and par can be converted using a Bridge scoring conversion table that converts a result to an International Match Point (IMP) scale. IMPs are typically used for scoring Bridge team events, therefore for events with this type of scoring, the comparison of par to DDA table result, or par to actual table result with a conversion to an IMP scale is more useful.

The LLN would apply given a large data set. There will be instances of a given pair playing against stronger, or weaker, opponents. Using the LLN, these factors should balance out of time. An optional enhancement to the method is using feedback loops. Applying the knowledge of how good/bad the opponents are based on the opponents' ratings and including this factor in the calculations.

The statistical analysis of bidding can be refined to particular subsets of the game. For example, in Bridge, one such class might be "weak twos" where a "two-level bid", which states the willingness to take 8 tricks with a certain suit as trumps, is made with a hand within a well-defined range. A collusive cheating pair may have an illegal agreement that if the bid is placed in the bidding tray a certain way it would indicate a bid on the low end of the range, and a bid placed another way would show a bid in the high end of the range. The opening bidder's partner can then re-evaluate their hand to determine if to proceed further with their auction or not. Analysis can be made examining only the set of hands where the partnership started the bidding with a weak two bid. There are many other such classes in bridge, for example "one no trump" opening bids, "two no trump" bids etc. Statistical analysis can show how effective a particular pair's class of bids are compared to others with similar methods.

Another example is the effectiveness of a partnership bidding to "game" or "slam" where additional points are available. Failing to bid a "game" or "slam" results in the loss of table result points.

Bridge Phase—Opening Lead

The opening lead is made in Bridge after the bidding phase. The opening lead is made without knowledge of the cards held by dummy. There are 13 possible choices for opening lead—any card from the opening leader's hand.

The opening lead can be tested against DDA to see if the lead gives up a trick. The number of times the opening lead does, or does not, give up a trick can be enumerated, and a statistical percentage created. Pairs have been known to cheat on the opening lead and signal their partner on the best suit to lead. The follow table shows the calculations of the top 75 players in top tournaments around the world. The Y axis shows the number of opening leads, the X axis is the average percentage of opening leads that do not give up a trick according to DDA. There is only one pair that is known to cheat on opening lead.

The average is 80.8%, with a standard deviation of approximately 3.0. If a pair is cheating, they are more likely to attempt to cheat on hands where the result, because off the scoring method used, is more valuable. This may make it necessary to further analyze the opening lead and break the data down into further subcategories. Examples of subcategories:

a. Leads against NT
b. Leads against suit contracts
c. Leads against game contracts
d. Leads against slam contracts
e. Leads against grand slam contracts
f. Leads against part scores
g. Leads when we are silent (our side does not bid)

Bridge Phase—Play of Hand—Played Cards Available

At everyone's turning to play, the card selected can be compared against DDA. One method is to enumerate the cards played that do not give up a trick against DDA and enumerate the cards played that do give up a trick against DDA. A simple percentage can then be calculated. This generates a rating value on how good a player or partnership is.

Another method is to apply a higher weighting to cards earlier in the play as there are more choices. An example is:

$$(DD1*13)\pm(DD2*12)\pm(DD3*11)+\ldots(DD12*2)/(T1*13)+(T2*12)+(T3*11)+\ldots(T12*2) \quad \text{—Equation 1—}$$

Where DDn is the number of times that the play was perfect double dummy for that trick number with the first trick being n=1 but excluding opening leads; and where T is the number of number of times the player played to that trick.

Another method is to examine the cards available to be played and calculate statistics based on the choices. For example, if a player only has one card in the suit led, that card must be played.

Using the LLN, the simplest formula is the percentage of cards that do not give up a trick, ignoring the opening lead. The phase can be broken down into defense and declarer.

Bridge Phase—Play of Hand (Defense)

The defensive play of the hand is the easiest for collusive cheating. Both players have multiple methods to illegally pass information. The following table is based on the top 60 pairs based on the amount of data available for each pair using one of the methods described in this patent. Only the first 8 pairs are listed. Only events with World Class competition are included. The pairs listed have been convicted of collusive cheating or have admitted to collusive cheating.

TABLE 4

| | Who | Defense |
|---|---|---|
| 1 | Lotan Fisher - Ron Schwartz | 98.43 |
| 2 | Adam Zmudzinski - Cezary Balicki | 98.38 |
| 3 | Entscho Wladow - Michael Elinescu | 98.36 |
| 4 | | 98.32 |
| 5 | | 98.23 |
| 6 | Alexander Smirnov - Josef Piekarek | 98.2 |
| 7 | | 98.19 |
| 8 | Claudio Nunes - Fulvio Fantoni | 98.19 |

The likelihood of these five cheating pairs appearing in the top 8 of a random list of 60 players can be calculated at about 1 in 100,000. No other pairs in the top 60 have been convicted of collusive cheating.

Bridge Phase—Play of Hand (Declarer)

Collusive cheating is far harder as declarer. It requires the dummy (the person opposite the partner), to signal information about the cards by either opponent. This requires dummy to peek into the hands. This is very easily detectable at the table.

The general approach can be applied to generate ratings for each player of a partnership as declarer. The declarer rating can be used as a performance indicator for how well a player would do when defending a hand. The declarer rating for both players can be combined, to generate an expected defender rating. If the expected defender rating does not match the actual defender rating, this is indicative that the pair may be cheating on defense.

Bridge Phase—Play of Hand—Played Cards Unavailable

If there is no data on the played cards, then we can use a coarser tool based on the contract and table result. One method is to record if the declarer made more than double dummy, the same as double dummy, or less than double dummy. Let's call these DDP, DDE, DDM (double dummy plus, equals or minus). We look at all boards that a pair has played. We started with DDP=DDE=DDM=0. For each board, either DDP, DDE or DDM is incremented.

We define the double dummy ratio (DDR) as DDP/DDM. This is a good indicator for rating a pair on defence. It is a good indicator for rating declarer play. DDR for all players remains fairly standard no matter the quality of opposition. Over time, pairs spend approximately as much time defending as declaring. If a strong pair is playing against a weaker pair, the weaker pair will be assumed to make more mistakes. These mistakes will occur both when defending a hand and when declaring a hand.

The DDR is fairly consistent for all pairs irrespective of the type of scoring and irrespective of the quality of the players. There are other formula could be used, e.g. DDP/(DDP+DDE+DDM). This formula tracks the percentage of times declarer makes more than double dummy. Expert defenders should expect a lower value. For declarer to make more than double dummy, the defenders have made a mistake during the play.

There are other formula could be used, e.g. DDM/(DDP+DDE+DDM). This formula tracks the percentage of times declarer makes less than double dummy. Expert defenders should expect a higher value. For declarer to make less than double dummy, declarer needs to make a mistake. Mistakes are expected as part of the game, using LLN each defending pair, assuming similar tournaments/opponents, should be the recipient of the same frequency of declarer mistakes as other pairs.

The DDR measures the ratio of the number of declarer and defensive mistakes.

Bridge Phase—Play of Hand (Defense)

The following table shows the DDR for the top 98 players with the most number of boards played from top tournaments. The X axis shows the DDR, the Y axis shows the number of boards. The lower a DDR the better the partnership, i.e. the fewer mistakes are made. The average is around 1.27 for all tournaments. Values further to the left indicate pairs who make fewer mistakes on defense.

The DDR can be used as a rating.

Statistics can be applied to the DDR to determine the deviation from normal expected values. These statistics can be used to determine the likelihood that this defensive rating is because of cheating.

For marketing or other purposes, a defensive rating can be generated for a pair based on various factors including the strength of the events that a pair plays in, time lag—i.e. dropping old events, weighting more recent events higher.

Separate ratings can be kept based on the level of competition. For example, the competition at World events is expected to be higher than competition at Club events.

A feedback loop can be created where the quality of the defense can be compared against the quality of the declarer.

For example, in 98 pairs, five can have been convicted or confessed to cheating in open events. All 5 have a DDR of equal to or under 0.86. There are only 10 pairs with a DDR of under 0.86. The probability of randomly selecting a rating method and having these 5 names appear in the top 10 is over 1 in 200,000. In other words, the DDR method can predict pairs likely to be cheating.

Conversely, using DDR it is possible to rule out someone as a likely collusively cheating pair. Or, that their cheating is so bad, that they should continue to do what they are doing because they are doing worse than pairs that do not cheat!

Bridge Phase—Play of Hand (Declarer)

There are various methods of calculating declarer skill. These methods include those listed under defense. For example, a declarer can be measured on their DDR.

Bridge Phase—Timing

Different aspects of a hand can be timed leading to analysis of how long it takes each player to make a decision. This can be fed into an algorithm to determine the likelihood of a player taking this amount of time to make that decision.

Bridge Data Aggregation

Data can be aggregated. For example, the DDR can be calculated for tournaments. Different tournaments can be compared against each other. Other statistical methods can be compared between tournaments.

Using DDR, or other methods, it is possible to calculate the deviation from expected norms and estimate the probability that there are cheating pairs playing in a tournament and to estimate the number of cheating pairs.

One method of comparing data is to compare the N/S DDR with the E/W DDR. Take for example the 2013, 2015, 2017 Bermuda Bowl (BB) (World Championship) and the 2014 European Bridge Team Championship (EBTC). Pairs since convicted of collusive cheating were playing in the 2013 BB and 2014 EBTC. If these pairs are removed from the data, the tournament's position moves to the right by 0.03 and 0.06 respectively.

The 2015 BB occurred after disclosure that pairs were cheating, and were caught using video evidence. It is believed that any pairs that might have been cheating did not cheat during this tournament as the perceived chance of being caught was high.

Rating System Summary

Embodiments described herein include methods and systems for improving statistics and cheating detection for use in partial knowledge and trick-taking games and tournaments, and more specifically to systems that can detect cheating for trick-taking game tournaments. This also includes the ability to rate players/partnerships in different aspects of the game. The embodiments also apply to games and tournaments that are partial knowledge events.

It is to be understood that both the foregoing general description and the following detailed description are exemplary and explanatory only and are not restrictive of the embodiments, as claimed.

Rating System

The system may also store historical results to help rate or handicap players in trick-taking games such as Bridge where handicaps previously were not possible. The system may track each bid and every card played in one embodiment.

In one embodiment, a processor executes instructions for measuring a player's skill during a board (one hand played in a tournament). Each time a player plays a card to a trick, there may be a limited number of cards they can play. For example, a game may require that they follow suit unless they are leading to a new trick (and then they can lead any suit). The system may perform a double dummy analysis (DDA) of the cards remaining so that the system can computationally work out the correct card (or cards) for someone to play. A DDA of a complete hand takes less than 1 second on a modern computer.

For each trick, the system may therefore determine if the player is playing the optimal or correct card (according to DDA), or, alternatively, is playing a card that will result in an inferior score. In this manner, the system may determine a performance value associated with each trick, and then analyze a total or average performance value over all the tricks in a given match, tournament, or historical period of time.

The system then may send each player a personalized rating of how well they did in a particular hand, match, or tournament. In one embodiment, the system automatically generates emails with the personalized results, which are emailed out to each participant.

As an example, Bridge is a 52 card 13 trick game where the system may create personalized ratings in one embodiment.

An example, shown below, is a famous hand that decided a National event based on an appeal which was partly based on how well each player played the hand. In this example, East is trying to take at least 9 tricks with no trumps.

TABLE 5

|  | North<br>♠ J98<br>♥ KQ3<br>♦ K8<br>♣ AJ932 |  |
|---|---|---|
| West<br>♠ 53<br>♥ A76<br>♦ AQJ975<br>♣ 107 |  | East<br>♠ AQ76<br>♥ J82<br>♦ 32<br>♣ KQ64 |
|  | South<br>♠ K1042<br>♥ 10954<br>♦ 1064<br>♣ 85 |  |

The system may assume perfect play by each side; that is, the system may assume that each player will play the card that will maximize the number of tricks for their side. The system may further rank cards from worst to best in their respective ability to maximize the number of tricks taken, and score based on the card selected.

In the example of the hand above, South is on lead at trick 1. If South leads a spade, then assuming perfect play by both sides, East will take 9 tricks. If South leads a heart, then assuming perfect play by both sides, East will take 7 tricks. If South leads a diamond or club, East will take 8 tricks (the words "perfect play" are assumed for the rest of this example). Thus, South has a set of cards which will generate the best possible score (in this example, for trick 1 it is a heart). There may be a different set of cards, possibly null, that will produce worse results (for example a club or diamond), and other sets of cards that will produce worse results.

The system may, therefore, rank South's opening lead compared to the best lead possible. The best lead is a heart. This same ranking system may recalculate ranking values for each play, until the first 48 cards are played (i.e., the last four cards are played by default).

Continuing with the example, if the South leads with the 8 of clubs, the processor may calculate that this is not the best card to play and may assign a lower numerical value to that play. Successive plays may be similarly analyzed. In one embodiment, the numerical value assigned to each play is based on the overall impact to the number of tricks taken. For example, when South leads with the 8 of clubs, this may do more damage to the number of possible tricks than any other successive play possibly could. So even if the successive plays are optimal, the processor may more heavily weigh the errant first play than any potential deviation in later play in determining the overall score. Similarly, in the game of Hearts, if a particular play causes a player to take the Queen of Spades and/or fail to shoot the moon, the processor may weigh that particular play more negatively.

Similarly, in the example above, it does not matter what card West plays to trick one after the 8 of clubs lead. The processor may use double dummy analysis (DDA) in one embodiment to make this decision. For plays where selection is immaterial, the algorithm may take this into account by not affecting the scoring positively or negatively in relation to the other plays that are consequential.

Continuing with the example, North now has a choice of five cards to play to the first trick. If North plays the Ace, then East can take 9 tricks. If North plays any other club, East's best effort is 8 tricks. The processor may therefore rank North's play to this trick. North has 5 choices. One is bad (Ace), while the other four have the same effect. The rating may be based on the number of choices North has, and the effect of the choice made.

After the Ace of clubs is played, East's best play is either the 6 or 4 of clubs. In both cases, East will now take 9 tricks. If East, however, plays the King or Queen of Clubs, then East's best effort is 8 tricks. So East has 4 choices, 2 of them are optimal, the other 2 are not. East chooses to play the 4 of clubs.

After the first trick, the processor may rate each person's play. Each play may be entered via a scoring device or a portable device such as a cell phone. The ratings may be computed at a server in one embodiment and withheld from the players until after the match is over in one aspect.

In this example, South made a choice that was not optimal (it gave up a trick), but it was not as bad as other choices could have been. West's choice was immaterial. North had 5 choices and picked the only card out of 5 that was bad. East had 4 choices, 2 optimal, 2 not.

Therefore, after the first trick, the processor may determine that East is on lead as East won the trick with the Ace of Clubs. DDA may show that the contract of nine tricks with no trumps can now be made. The Jack of Clubs, or a spade will hold East to nine tricks (four choices). A diamond will give East eleven tricks (two choices). A heart or any other club will give East ten tricks (six choices).

Continuing, North chooses to play the King of Hearts. We can rate North based on having twelve choices and making a non-optimal choice when four better choices were available. After the King of Hearts if played, East then has 3 choices. The worst is the Jack of Hearts, giving up two tricks. East chooses the two of hearts. South's choice is immaterial. South plays the 4 of hearts. West now has a choice. If West plays the Ace of Hearts, this is the optimal play and guarantees 10 tricks. The 7 or 6 of hearts guarantees 8 tricks. West chooses the 6 of hearts.

The spotlight now returns to North. West made a bad play, North can now set the contract of 9 tricks with no trumps by playing a spade. North has 11 choices. 3 are good (spades), one is bad (Jack of Clubs) giving up one trick, 5 are worse (any other club or heart) giving up two tricks, a diamond is even worse, giving up 3 tricks. North played the queen of hearts. A bad play according to double dummy analysis.

The system may continue this process until all 13 tricks have been played. The processor may then examine each player's decision for the first 12 tricks and determine how good their choice was, compared to double dummy analysis in one embodiment. The processor may then determine how well each player made the optimal choice. The specific algorithm for each event can be modified based on the scoring method used.

Ratings from different aspects of a bridge game: bidding, opening lead, defensive play, declarer play can be combined to create a single rating for a player. The ratio of weighting to apply to each phase is arbitrary. For example, one weighting may be 35% bidding, 5% opening lead, 30% declarer play excluding opening lead, 30% defensive play. The formula for each of the phases is also arbitrary as there are multiple methods of rating. One such formula may be to use bidding against par for the bidding, percentage of opening leads that do not give up a trick, percentage of cards played that do not give up a trick.

Alternatively, not all of this information may be available. For example, tracking of each card played is currently rare. An alternate is to rate the declarer play and defensive play based on final outcome as compared to DDA.

The ratings can be used to create rankings for the best player.

Ratings can be divided by class of event, e.g. Women, Senior, Open, Youth.

Ratings can be divided by type of event, e.g. Pairs, Teams

Ratings can be divided by quality of event, e.g. World, National, Regional, Sectional, Club.

What is claimed is:

1. A system for detecting cheating players in a card game, including:
   a non-transitory, computer-readable medium containing instructions; and
   a processor that executes the instructions to perform stages comprising:
   acquiring board data for multiple events, the events including bridge games, wherein the board data corresponds to boards in the bridge games, and wherein the board data includes hand records, a table result, contract, and declarer from the respective bridge game;
   for multiple of the boards in each event, determining performance values for a player of the respective board based on the board data and timing information, wherein the timing information conveys how long the player took to make a call or play a card during the event;
   detecting, by the processor, a deviation by comparing the performance values from a first event against a threshold, wherein the threshold is based on at least one of past performance of known cheating players and optimal bridge behavior, wherein the optimal bridge behavior is based on performance values for non-cheating players from the multiple events; and
   alerting an administrative user for the first event regarding a likelihood of cheating when the deviation is detected, wherein the alert includes automatically sending an electronic message to the administrative user.

2. The system of claim 1, wherein acquiring the board data includes crawling a website that displays bridge tournament results, and wherein names acquired from the crawling are normalized.

3. The system of claim 1, the stages further comprising determining a skill level rating for the player based on a contract and comparison of that contract to a most possible number of tricks taken, wherein the threshold is based on the skill level rating.

4. The system of claim 1, the stages further comprising determining a skill level rating for each player based at least in part on whether a card played by each player took more, the same, or fewer tricks than a predicted number based on all cards for all of the players at the beginning of a board in the event.

5. The system of claim 1, wherein detecting the deviation includes comparing declarer ratings and records for two players with partnership defensive rating and records for those two players.

6. The system of claim 1, wherein detecting the deviation includes comparing against a threshold for improper partnership agreements.

7. The system of claim 1, wherein the performance values are determined for a partnership that includes the player.

8. The system of claim 1, the stages further comprising detecting metal deterioration based on a change in double dummy ratio ("DDR") values for the player, indicating a loss in playing ability.

9. The system of claim 1, the stages further comprising:
   detecting mental deterioration based on a change in double dummy calculations based on played cards for the player, indicating a loss in playing ability; and
   detecting cheating based on a sudden value increase based on in double dummy calculations for played cards by the player, indicating a loss in playing ability.

10. A method for detecting cheating players in a card game, comprising:
    acquiring, by a processor board data for multiple events, the events including bridge games, wherein the board data corresponds to boards in the bridge games, and wherein the board data includes hand records, a table result, contract, and declarer from the respective bridge game;
    for multiple of the boards in each event, determining performance values for a player of the respective board based on the board data and timing information, wherein the timing information conveys how long the player took to make a call or play a card during the event;
    detecting, by the processor, a deviation by comparing the performance values from a first event against a threshold, wherein the threshold is based on at least one of past performance of known cheating players and optimal bridge behavior, wherein the optimal bridge behavior is based on performance values for non-cheating players from the multiple events; and
    alerting an administrative user for the first event regarding a likelihood of cheating when the deviation is detected, wherein the alert includes automatically sending an electronic message to the administrative user.

11. The method of claim 10, further comprising determining a skill level rating for the player based on a contract and comparison of that contract to a most possible number of tricks taken, wherein the threshold is based on the skill level rating.

12. The method of claim 10, further comprising determining a skill level rating for each player based at least in part on whether a card played by each player took more, the same, or fewer tricks than a predicted number based on all cards for all of the players at the beginning of a board in the event.

13. The method of claim 10, wherein detecting the deviation includes comparing declarer ratings and records for two players with partnership defensive rating and records for those two players.

14. The method of claim 10, wherein detecting the deviation includes comparing against a threshold used to indicate improper partnership agreements.

15. The method of claim 10, wherein the performance values are determined for a partnership that includes the player.

16. The method of claim 10, further comprising detecting onset of Alzheimer's based on a change in double dummy ratio ("DDR") values for a player, indicating a loss in playing ability.

17. A non-transitory, computer-readable medium including instructions for detecting cheating players in a card game, wherein the instructions are executed by a processor to perform stages comprising:
    acquiring board data for multiple events, the events including bridge games, wherein the board data corresponds to boards in the bridge games, wherein the board data includes hand records, a table result, contract, and declarer from the respective bridge game;
    for multiple of the boards in each event, determining performance values for a player of the respective board based on the board data and timing information, wherein the timing information conveys how long the player took to make a call or play a card during the event;

detecting, by the processor, a deviation by comparing the performance values from a first event against a threshold, wherein the threshold is based on at least one of past performance of known cheating players and optimal bridge behavior, wherein the optimal bridge behavior is based on performance values for non-cheating players from the multiple events; and alerting an administrative user for the first event regarding a likelihood of cheating when the deviation is detected, wherein the alert includes automatically sending an electronic message to the administrative user.

18. The non-transitory, computer-readable medium of claim 17, wherein acquiring the board data includes crawling a website that displays bridge tournament results, and wherein names acquired from the crawling are normalized.

19. The non-transitory, computer-readable medium of claim 17, further comprising determining a skill level rating for the player based on a contract and comparison of that contract to a most possible number of tricks taken, wherein the threshold is based on the skill level rating.

20. The non-transitory, computer-readable medium of claim 17, wherein detecting the deviation includes comparing declarer ratings and records for two players with partnership defensive rating and records for those two players.

* * * * *